United States Patent
Hersh et al.

(10) Patent No.: US 7,544,167 B2
(45) Date of Patent: Jun. 9, 2009

(54) METHOD AND SYSTEM FOR CUFF PRESSURE REVERSIONS

(75) Inventors: Lawrence T. Hersh, Tampa, FL (US); Richard Medero, Tampa, FL (US); Bruce A. Friedman, Tampa, FL (US); Sai Kolluri, Tampa, FL (US)

(73) Assignee: GE Medical Systems Information Technologies, Inc., Milwaukee, WI (US)

( * ) Notice: Subject to any disclaimer, the term of this patent is extended or adjusted under 35 U.S.C. 154(b) by 220 days.

(21) Appl. No.: 11/626,170

(22) Filed: Jan. 23, 2007

(65) Prior Publication Data

US 2007/0129638 A1 Jun. 7, 2007

Related U.S. Application Data

(62) Division of application No. 10/375,409, filed on Feb. 27, 2003, now Pat. No. 7,186,218.

(51) Int. Cl.
*A61B 5/02* (2006.01)
(52) U.S. Cl. ........................... 600/494; 600/490
(58) Field of Classification Search .............. 600/481, 600/483, 485, 490–503
See application file for complete search history.

(56) References Cited

U.S. PATENT DOCUMENTS

| | | | |
|---|---|---|---|
| 4,349,034 A * | 9/1982 | Ramsey, III .................. 600/494 |
| 4,360,029 A | 11/1982 | Ramsey, III | |
| 4,543,962 A | 10/1985 | Medero et al. | |
| 4,638,810 A | 1/1987 | Ramsey, III et al. | |
| 4,729,383 A * | 3/1988 | Susi ............................ 600/494 |
| 4,796,184 A | 1/1989 | Bahr et al. | |
| 4,889,133 A | 12/1989 | Nelson et al. | |
| 4,926,873 A | 5/1990 | Frankenreiter | |
| 4,949,710 A | 8/1990 | Dorsett et al. | |
| 5,052,397 A * | 10/1991 | Ramsey et al. ............... 600/495 |
| 5,054,494 A * | 10/1991 | Lazzaro et al. ............... 600/490 |
| 5,170,795 A * | 12/1992 | Ramsey et al. ............... 600/495 |
| 5,243,990 A | 9/1993 | Aung et al. | |
| 5,542,428 A * | 8/1996 | Jayne .......................... 600/494 |
| 5,579,776 A | 12/1996 | Medero | |
| 5,590,662 A * | 1/1997 | Hersh et al. .................. 600/494 |
| 5,653,241 A | 8/1997 | Harada et al. | |
| 5,704,362 A | 1/1998 | Hersh et al. | |
| 6,358,213 B1 | 3/2002 | Friedman et al. | |
| 6,423,010 B1 | 7/2002 | Friedman et al. | |
| 6,440,080 B1 | 8/2002 | Booth et al. | |
| 6,702,753 B2 | 3/2004 | Nunome | |
| 6,893,403 B2 * | 5/2005 | Kolluri et al. ............... 600/494 |
| 7,186,218 B2 | 3/2007 | Hersh et al. | |
| 2002/0082507 A1 | 6/2002 | Kolluri et al. | |

* cited by examiner

*Primary Examiner*—Charles A Marmor, II
*Assistant Examiner*—Navin Natnithithadha
(74) *Attorney, Agent, or Firm*—Andrus, Sceales, Starke & Sawall, LLP

(57) ABSTRACT

A method and system for determining when to make a reversion to smaller cuff pressure steps during an oscillometric blood pressure measurement is disclosed. The method and system comprise comparing conformance of oscillometric envelope blood pressure data with previous blood pressure data, including measuring a shift between the oscillometric envelope blood pressure data and an oscillometric envelope derived from the previous blood pressure data. In addition, the method and system include making a reversion decision based on whether the shift exceeds an allowable threshold. Once a reversion decision is made a subsequent decision may be made as to the need for increasing the cuff pressure level.

15 Claims, 7 Drawing Sheets

METHOD AND SYSTEM FOR CUFF PRESSURE REVERSIONS

This application is a divisional application of application Ser. No. 10/375,409 filed on Feb. 27, 2003, now U.S. Pat. No. 7,186,218, which issued on Mar. 6 2007.

BACKGROUND OF THE INVENTION

The field of the invention is patient monitoring systems. More particularly, the invention relates to a method and system that uses previous blood pressure data to determine when to change the pressure step size during blood pressure readings.

The heart muscles of humans periodically contract to force blood through the arteries. As a result of this pumping action, pressure pulses exist in these arteries and cause them to cyclically change volume. The baseline pressure for these pulses is known as the diastolic pressure and the peak pressure for these pulses is known as the systolic pressure. A further pressure value, known as the "mean arterial pressure" (MAP), represents a time-weighted average of the blood pressure. The systolic, MAP and diastolic values for a patient are useful in monitoring the cardiovascular state of the patient, to diagnose a wide variety of pathological conditions, and treat disease. Therefore, it is a great advantage to a clinician to have an automatic device which can accurately, quickly and non-invasively estimate these blood pressure values.

There are different techniques and devices for measuring one or more of these blood pressure values. One method in particular involves applying an inflatable pressure cuff about the upper arm of a human and inflating it above systolic pressure so as to restrict the flow of blood in the brachial artery. The pressure is then slowly relieved while a stethoscope is used on the distal portion of the artery to listen for pulsating sounds, known as Korotkoff sounds, that accompany the reestablishment of blood flow in the artery. As the pressure in the cuff is reduced further, the Korotkoff sounds eventually disappear. The cuff pressure at which the Korotkoff sounds first appear during deflation of the cuff is an indirect measure of the systolic pressure and the pressure at which these sounds disappear is an indirect measure of the diastolic pressure. This method of blood pressure detection is generally known as the auscultatory method.

Another method of measuring blood pressure is referred to as the oscillometric technique. This method of measuring blood pressure involves applying an inflatable cuff around an extremity of a patient's body, such as the patient's upper arm. The cuff is inflated to a pressure above the patient's systolic pressure and then reduced over time while a pressure sensor continues to measure the cuff pressure. The sensitivity of the sensor is such that pressure fluctuations within the cuff resulting from the beats of the patient's heart may be detected. With each beat there is a resulting small change in the artery volume which is transferred to the inflated cuff causing slight pressure variations within the cuff which are detected by the pressure sensor. The pressure sensor produces an electrical signal showing the incremental cuff pressure and a series of small periodic variations associated with the beats of a patient's heart. It has been found that these variations, called "complexes" or "oscillations," have a peak-to-peak amplitude which is minimal for applied cuff pressures above the systolic pressure. As the cuff pressure is decreased, the oscillation size begins to monotonically grow and eventually reaches a maximum amplitude. After it reaches a maximum amplitude, the oscillation size decreases monotonically as the cuff pressure continues to decrease. Physiologically, the cuff pressure at the maximum value approximates the MAP. In addition, the complex amplitudes of cuff pressures equivalent to the systolic and diastolic pressures have a fixed relationship to this maximum value. Thus, the oscillometric method is based on measurements of detected complex amplitudes at various cuff pressures.

Blood pressure measuring devices operating according to the oscillometric method are used for detecting the peak-to-peak amplitude of the pressure complexes at various applied cuff pressure levels. The amplitudes of these complexes, as well as the applied cuff pressure, are stored together as the device automatically changes the cuff pressures over a range of interest. These peak-to-peak complex amplitudes define an oscillometric "envelope" and are evaluated to find the maximum value and its related cuff pressure, which is approximately equal to MAP. A cuff pressure below the MAP value which produces a peak-to-peak complex amplitude having a certain fixed relationship to the maximum value, is designated as the diastolic pressure. Likewise, a cuff pressure above the MAP value which results in complexes having an amplitude with a certain fixed relationship to that maximum value is designated as the systolic pressure. The ratios of complex amplitude at systolic and diastolic pressures to the maximum complex amplitude at MAP, are empirically derived and assume varying levels depending on the preferences of those of ordinary skill in the art. Generally, these ratios are designated in the range of 40% to 80%.

One way to determine estimates of blood pressure is to computationally fit a curve to the oscillometric envelope defined by the complex amplitude versus cuff pressure data points which are measured by a blood pressure monitor during a determination. The fitted curve may then be used to compute an estimate of the MAP value, which is approximately at the maximum value of the fitted curve and is therefore easily determined by finding the point on the fitted curve at which the first derivative equals zero. From this maximum value data point, the systolic and diastolic pressures may be computed by finding fixed percentages of the maximum complex amplitude on the curve and using the associated cuff pressure levels as the systolic and diastolic estimates. In this manner, indirect estimates of the systolic, MAP and diastolic arterial pressures may be found and ultimately output by an oscillometric device. The curve fitting technique has the value of smoothing the envelope information so that artifact variations are minimized and no single point dominates in the calculation of blood pressure, thereby resulting in more accurate estimates.

Usually, when taking an oscillometric blood pressure determination, a device will pump up to a supra-systolic cuff pressure level and take small deflation steps in order to completely measure the properties of the oscillometric envelope. However, pumping to higher than necessary cuff pressure levels and taking smaller than necessary steps may cause patient discomfort. Discomfort often results in patient motion which increases the likelihood of artifact, especially in pediatric and neonatal patients. Increased motion artifact may cause a non-determination or delay information output to the clinician. Therefore, to enhance patient comfort and reduce determination time, it is often desirable to take blood pressure readings with a minimal number of pressure steps. The oscillometric envelope pattern is simple and by judiciously choosing the particular cuff pressure levels to visit, the number of steps needed to compute an accurate blood pressure can be significantly lowered. This involves making decisions about what cuff pressure levels to visit based on the measurements and results of previous blood pressure determinations. It is generally known in the art that by visiting key points around the systolic, MAP and diastolic pressure levels, an accurate blood pressure can be estimated without the need to fill out every characteristic of the oscillometric envelope. Thus, the initial cuff pressure and size of the steps with which to deflate the cuff can be optimized if a previous blood pressure determination has been made and the blood pressure has not changed significantly. This means that the deflation steps will be much bigger than what would be used if the blood pressure were not known. Typically, these larger cuff pressure steps can be in the range of 12 to 20 mm Hg and are chosen so as to go to specific cuff pressure levels based primarily on the systolic, MAP, and diastolic pressure values of the previous determination. Since it is necessary for a patient's blood pressure to remain substantially similar to the previous determination before the accelerated inflation and deflation scheduling can be undertaken, the algorithm must have a means of guaranteeing that the blood pressure has not significantly changed. In situations where the blood pressure has significantly changed or is changing, it becomes necessary to return to a cuff deflation scheme in which the step sizes are smaller so that the details of the oscillometric envelope will be captured. Very often, these smaller cuff pressure steps are in the range of 2 to 8 mm Hg. In these circumstances, the act of returning to a different cuff pressure deflation scheme with smaller cuff pressure steps in order to obtain the full range and detail of oscillometric envelope data is called a reversion. Oftentimes, it is difficult to quickly and accurately determine when a reversion should be made. Thus, there exists a need for a method and system for quickly and effectively determining when to make a reversion to smaller cuff pressure steps and whether to increase or decrease cuff pressure during the reversion based on previous blood pressure determinations.

SUMMARY OF THE INVENTION

One embodiment of the present invention provides a method of determining when to make a reversion to smaller cuff pressure steps during an oscillometric blood pressure measurement. The method includes comparing conformance of oscillometric envelope blood pressure data with previous blood pressure data, including measuring a shift between the oscillometric envelope blood pressure data and an oscillometric envelope derived from the previous blood pressure data. In addition, the method includes making a reversion decision based on whether the shift exceeds an allowable threshold.

Another embodiment of the present invention provides a method of determining when to make a reversion to smaller cuff pressure steps during an oscillometric blood pressure measurement comprising comparing conformance of oscillometric envelope blood pressure data with previous blood pressure data, which includes evaluating whether oscillometric envelope amplitudes exceed an allowable tolerance from the previous blood pressure data. In addition, the method includes making a reversion decision based on whether the oscillometric envelope amplitudes exceed the allowable tolerance.

Another embodiment of the present invention provides a method of determining when to make a reversion to smaller cuff pressure steps during an oscillometric blood pressure measurement including evaluating whether an oscillometric envelope acquisition process has been completed and making a reversion decision based on whether the envelope acquisition process has been completed.

Another embodiment of the present invention provides an apparatus for measuring blood pressure including an inflatable cuff, a pressurizing apparatus, a cuff pressure sensor, and a programmed control device. The pressurizing apparatus is coupled to the cuff for selectively applying pressure by inflating or deflating the cuff. The cuff pressure sensor is coupled to the cuff for sensing cuff pressure and blood pressure oscillations. Further, the programmed control device controls the pressure cuff and pressurizing apparatus, compares conformance of oscillometric envelope blood pressure data with previous blood pressure data, including measuring a shift between the oscillometric envelope blood pressure data and an oscillometric envelope derived from the previous blood pressure data, and makes a reversion decision based on whether the shift exceeds an allowable threshold.

Another embodiment of the present invention provides a system for determining when to make a reversion to smaller cuff pressure steps during oscillometric envelope blood pressure determinations including a means for comparing conformance of oscillometric envelope blood pressure data with previous blood pressure data, including measuring a shift between the oscillometric envelope blood pressure data and an oscillometric envelope derived from the previous blood pressure data. In addition, the system includes a means for making a reversion decision based on whether the shift exceeds an allowable threshold.

Another embodiment of the present invention provides a computer program product comprising a computer useable medium having computer logic for enabling at least one processor in a computer system to determine when to make a reversion to smaller cuff pressure steps during oscillometric envelope blood pressure determinations. In addition, the computer program product includes a means for comparing conformance of oscillometric envelope blood pressure data with previous blood pressure data, including measuring a shift between the oscillometric envelope blood pressure data and an oscillometric envelope derived from the previous blood pressure data. Furthermore, the computer program product includes a means for making a reversion decision based on whether the shift exceeds an allowable threshold.

DESCRIPTION OF THE PREFERRED EMBODIMENT

Figure 1:
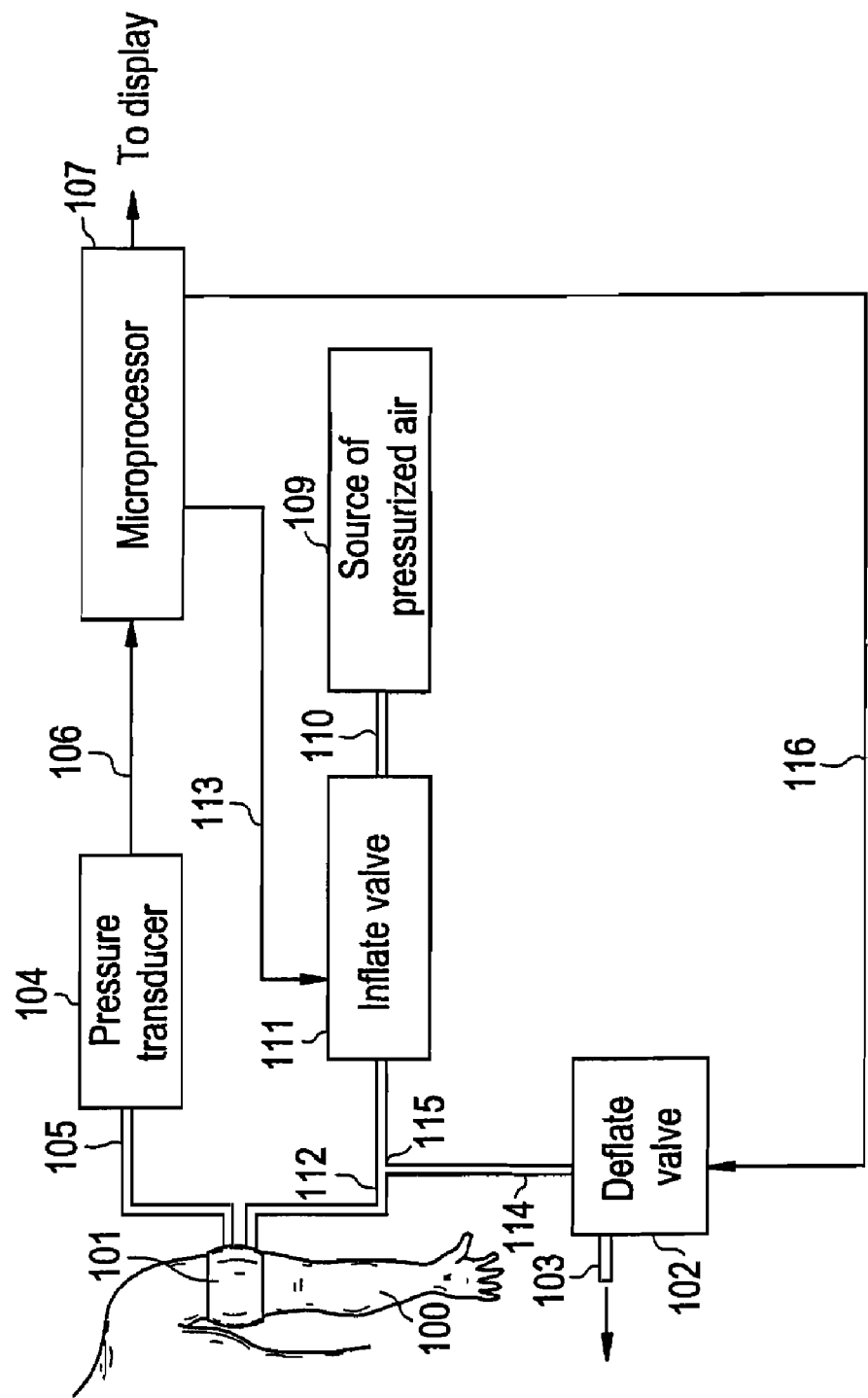
FIG. 1 is a diagram of a non-invasive blood pressure monitoring system in accordance with an embodiment of the present invention.

FIG. 1 shows the arm of a human subject wearing a conventional flexible inflatable and deflatable cuff 101 for occluding the brachial artery when fully inflated. As cuff 101 is deflated using deflate valve 102 having exhaust 103, the arterial occlusion is gradually relieved. The deflation of cuff 101 via deflate valve 102 is controlled by microprocessor 107 via control line 116.

A pressure transducer 104 is coupled by a hose or duct 105 to the cuff 101 for sensing the pressure therein. In accordance with conventional oscillometric techniques and due to the compliant properties of the blood vessels, pressure oscillations in the artery caused by a heart beat result in small cyclical volume changes in the artery. These small volume changes in the artery are transferred to the inflated cuff wrapped around the limb and finally result in small pressure changes in the cuff 101. These cuff pressure oscillations are sensed by pressure transducer 104 and converted into an electrical signal and coupled over path 106 to microprocessor 107 for processing. In addition, a source of pressurized air 109 is connected via a duct 110 through an inflate valve 111 and a duct 112 to the pressure cuff 101. The inflate valve 111 is electrically controlled through a connection 113 from the microprocessor 107. Also, the deflate valve 102 is connected by duct 114 via a branch connection 115 with the duct 112 leading to cuff 101. This deflate valve 102 is normally closed during the inflation process and is briefly opened by a deflate control mechanism to provide the pressure step levels where cuff oscillations are detected.

Figure 2:
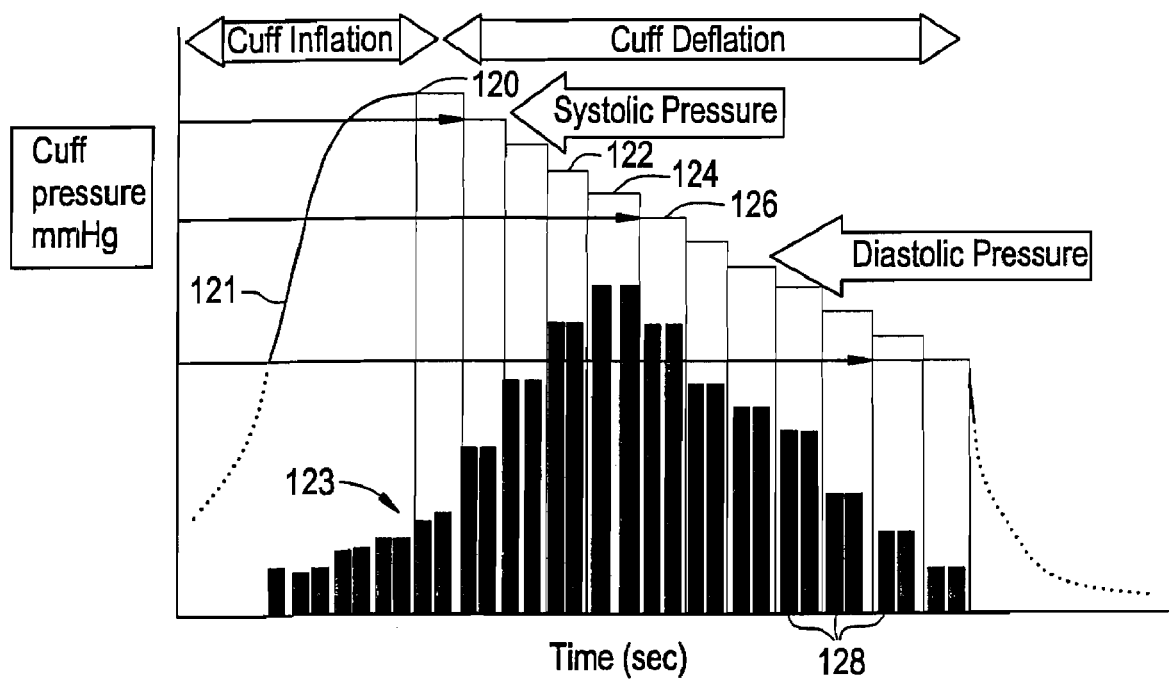
FIG. 2 displays typical waveforms for a normal oscillometric non-invasive blood pressure determination with amplitude of oscillometric pulses shown as a function of time.

FIG. 2 displays typical waveforms for a normal oscillometric non-invasive blood pressure determination with amplitude of oscillometric pulses gathered at different cuff pressures. Two waveforms are shown. Curve 121 represents the overall cuff pressure of the inflatable cuff and curve 123 represents the measured pulse amplitudes for oscillometric complexes at various cuff pressures as time through the determination progresses. Curves 121 and 123 can be used to construct an oscillation amplitude versus cuff pressure curve which is known as the oscillometric envelope. As can be seen, the cuff is first inflated to a supra-systolic pressure 120, and then reduced in a series of small incremental steps, such as steps 122, 124, 126. Oscillations 128 corresponding to each pulse are measured at each incremental cuff pressure. The peak pulse amplitudes (PPA) of each oscillation increase with each decrement of cuff pressure until the PPA reaches a maximum at cuff pressure 124. The PPA diminishes with every subsequent reduction in cuff pressure. Thus, the cuff pressure at step 124 represents the patient's MAP, and the patient's systolic and diastolic pressures can be determined therefrom. Although FIG. 2 shows incremental decreases in pressure steps, similar determinations as those above may also be made from continuous or linear decreases in pressure over time rather than incremental steps.

Figure 3:
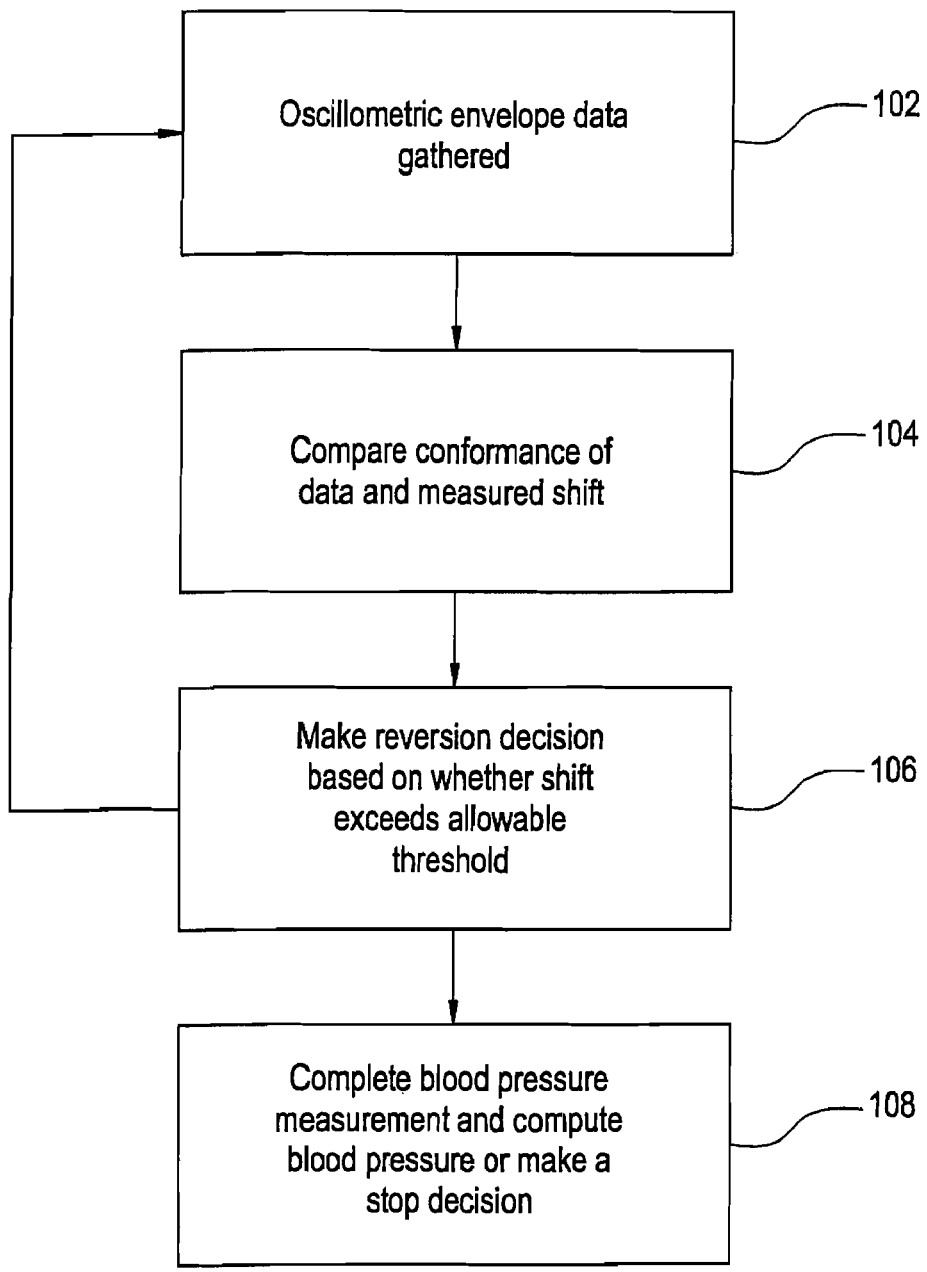
FIG. 3 is a summary flow chart showing a process for measuring blood pressure according to an embodiment of the present invention.

Referring to FIG. 3, a general flow chart representing a process for determining blood pressure is shown. Process 100 shows a method of determining when to make a reversion to smaller cuff pressure steps during oscillometric blood pressure measurements based on the existence of a previous blood pressure determination. First, measurements of blood pressure complexes are obtained to determine the oscillometric envelope at step 102. The measurements are initially obtained using relatively larger pressure steps. At step 104, a comparison is made for the conformance of oscillometric envelope blood pressure data with previous blood pressure data. This includes measuring a shift between the oscillometric envelope blood pressure data and an oscillometric envelope derived from the previous blood pressure data. At step 106, a reversion decision is made based on whether the shift exceeds an allowable threshold. Finally, the blood pressure measurement is completed using relatively smaller steps and blood pressure is computed at step 108. Alternatively, a stop decision is made at step 108.

Figure 4A:
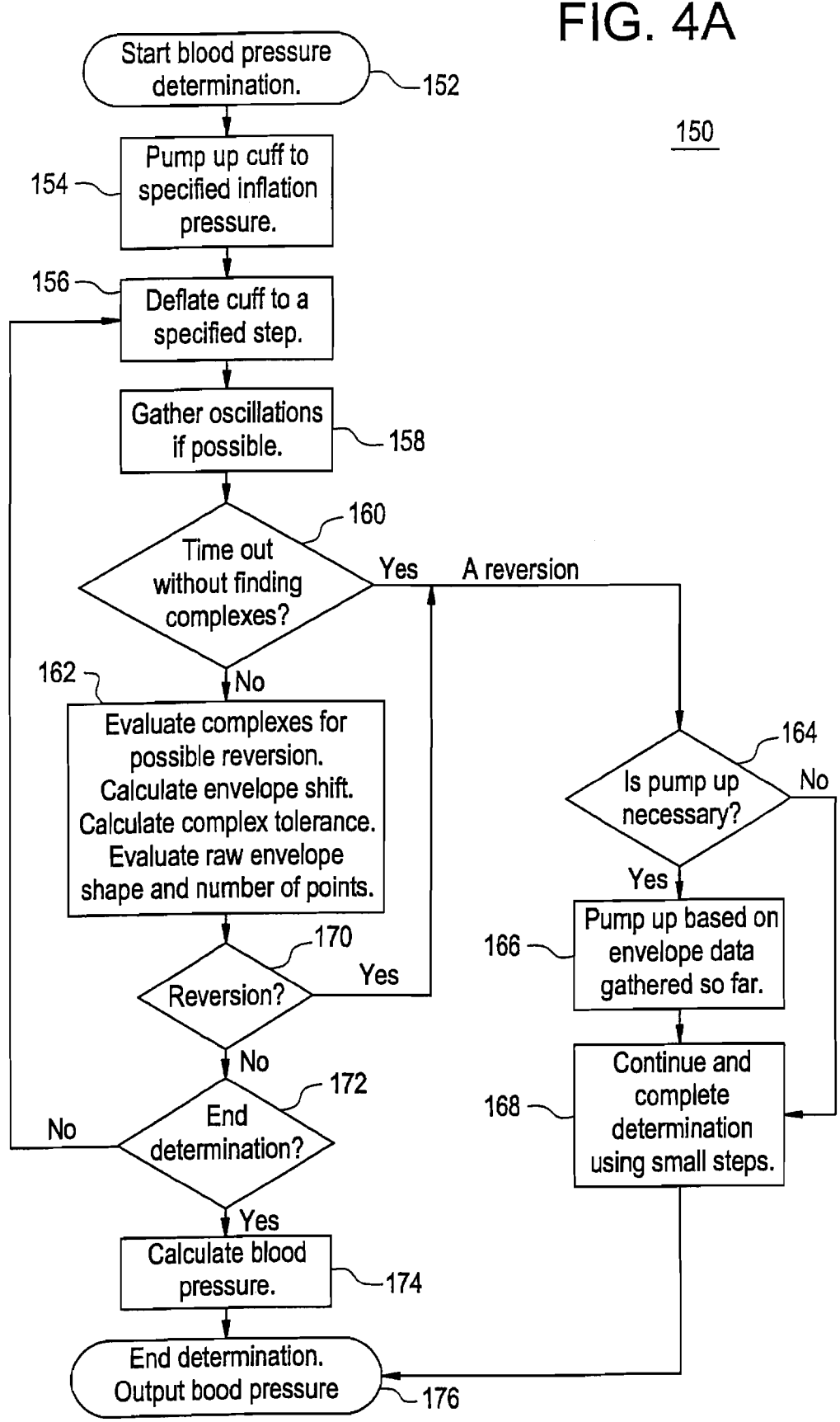
FIG. 4A is a detailed flow chart showing a process for measuring blood pressure according to an embodiment of the present invention.

FIG. 4A is a detailed flow chart showing process 150 for determining when to make a reversion decision during a blood pressure determination. The process begins at step 152 and pumps up the cuff to a specified inflation pressure for the particular patient as is generally known in the art. As is usually the case, the first cuff pressure is set greater than the previous systolic pressure. Next, the cuff is deflated at step 156 to a specified pressure. Oscillations are gathered at step 158 if possible. At step 160, it is determined whether the process times out without finding complexes. If the process times out, a reversion has taken place and it is determined whether a pump up in pressure is required at step 164. If the pump up is not necessary, the process continues to step 168 and completes the blood pressure determination using small steps. If the pump up is necessary at step 164, a pump up occurs at step 166 based on the oscillometric envelope data gathered go far. Then the process goes to step 168. After step 168, the process would end the determination and output the blood pressure.

Referring back to step 160 in FIG. 4A, if there was not a time out in finding complexes, the process proceeds to step 162. At step 162, the complexes are evaluated for a possible reversion. The criteria evaluated for a possible reversion includes: identifying the oscillometric envelope shift, verifying that the complexes are within the predetermined tolerance, evaluating the shape of the raw oscillometric envelope, and verifying that there are enough points on either side of the oscillometric envelope. After step 162, the process determines if a reversion should occur. If so, the process proceeds to step 164 as described above. Otherwise, the process analyzes whether to end the determination at step 172. If more data is required, the process returns to step 156. However, if there is enough data, the process proceeds to step 174 and determines blood pressure. Finally, the process outputs the blood pressure at step 176.

Figure 4B:
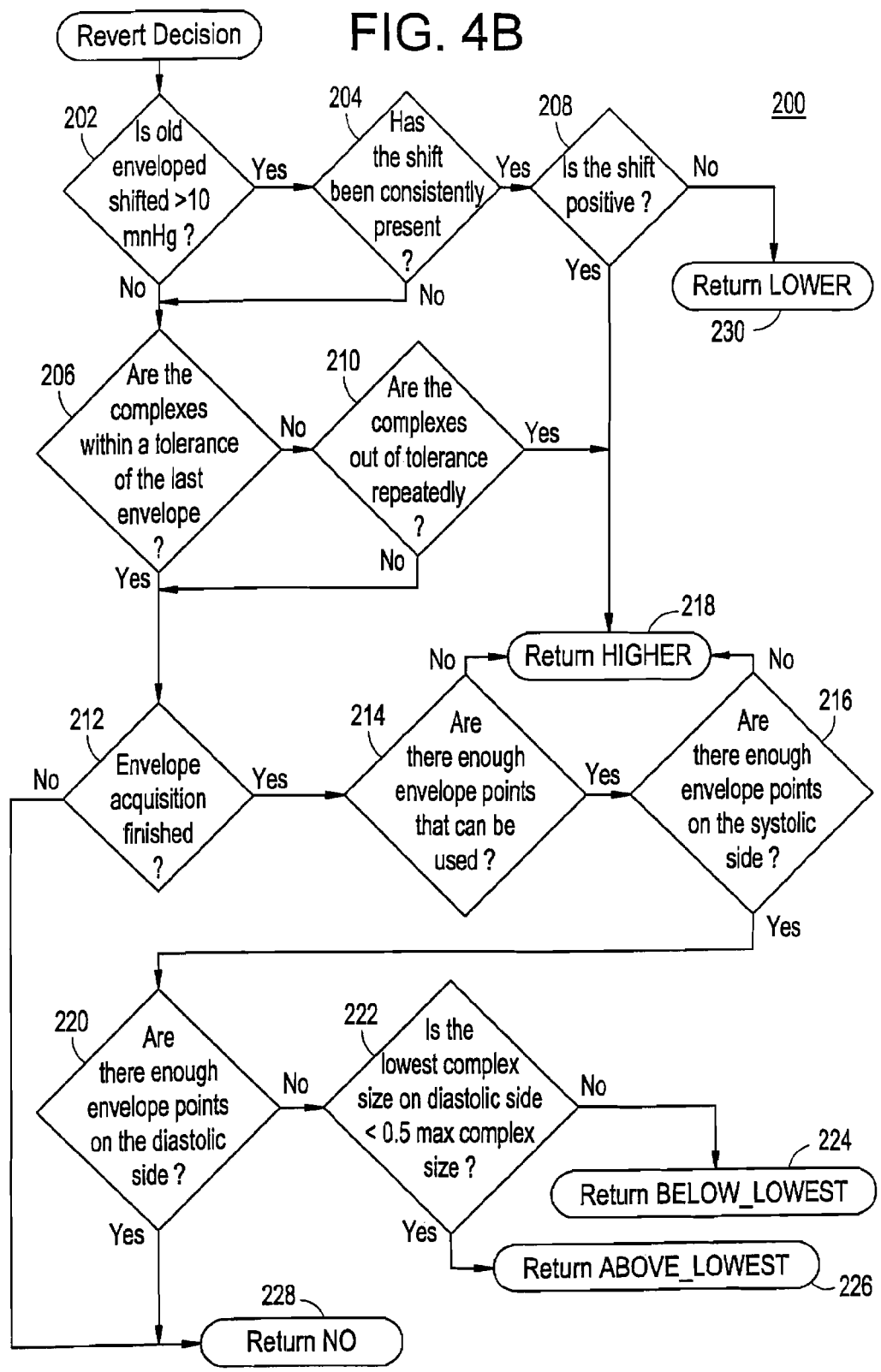
FIG. 4B is a flow chart showing a process for measuring blood pressure using curve fit information involving reverting and searching techniques according to an embodiment of the present invention.
Figure 5:
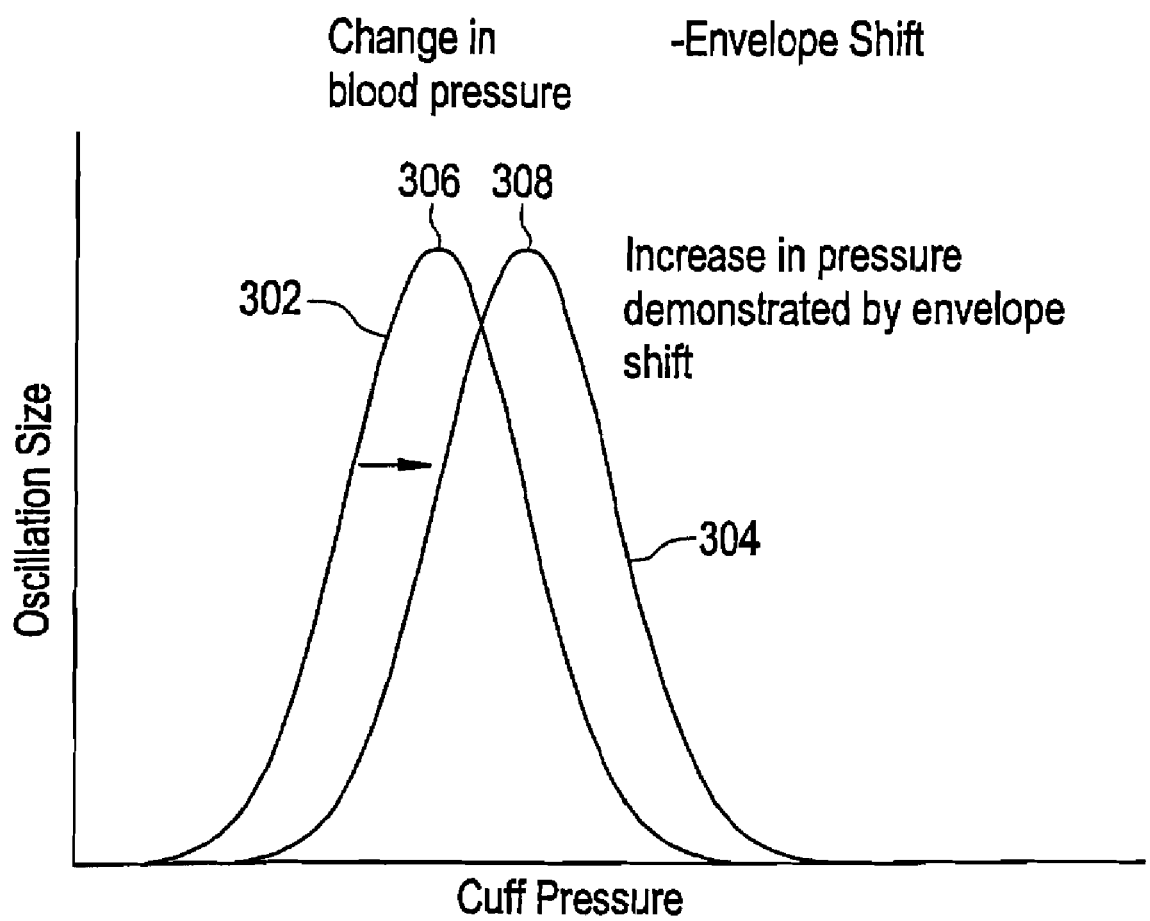
FIG. 5 illustrates a shift in an oscillometric envelope due to a change in blood pressure according to an embodiment of the present invention.

Referring to FIG. 4B, a flow chart is provided that shows certain steps and criteria for making a reversion decision during a blood pressure determination. The basic underlying assumption for process 200 is that a prior oscillometric envelope derived from previous measurements already exists. The previous oscillometric envelope and its associated curvefit parameters are then used in evaluating the current oscillometric data and to help determine whether a reversion needs to be made. For example, a method of employing curvefit parameters is described in U.S. Pat. No. 5,704,362 to Hersh et al. The current oscillometric envelope data, if on the same patient and within a reasonable time period, is expected to have the same relationship between the oscillation amplitude and the associated cuff pressure as the previous blood pressure determination. Therefore, new oscillation data points are expected to compare favorably to those predicted by the curvefit from the previous determination if there has not been a significant change in blood pressure. This type of comparison occurs at step 202. An example of a shift in the oscillometric curve is shown in FIG. 5. The initial oscillation curve is indicated by curve 302 and the shifted curve is indicated by curve 304. The difference in cuff pressure between the two data sets, which is an indication of envelope shifting, can be measured from point 306 to point 308. An envelope shift will result if there is a noticeable change in the blood pressure of a patient. However, there has to be some tolerance in making the decision to revert since it is not necessary to do so if there are only small changes in the complex amplitudes unrelated to blood pressure. In situations, where blood pressure has changed, process 200 provides mechanisms to ensure accurate blood pressure values. The mathematical technique for shifting the blood pressure envelope as measured in the previous determination to the blood pressure of the present determination uses the principle of aligning the previously determined curve with the complex amplitudes measured during the current determination. The shift that results after aligning the new data with the curve from the previous determination is an estimate of how much the blood pressure has changed. This indication of change or shift can be used to decide, or at least influence, the decision of whether or not to make a reversion. As this shift becomes large, it is less likely that the envelope characteristic will be measured well enough to accurately determine the blood pressure. At this point, it is best for the controlling algorithm to cause a reversion (and pump up if necessary) and find the oscillation sizes using much smaller pressure steps.

Referring back to FIG. 4B, at step 202, the controller determines whether the old envelope has to be shifted more than 10 mm of Hg to match the current data. In other words, an evaluation is made whether the difference between points 306, 308 on FIG. 5 is greater than a 10 mm Hg threshold. Of course, the use of 10 mm Hg is merely exemplary and any number of other limits could also be used (e.g., 9 mm Hg, 11 mm Hg, etc.). If there has not been a shift of more than 10 mm Hg, the process determines whether the complexes in the current determination are within a tolerance of the last envelope at step 206. According to an embodiment of the present invention, this tolerance requires the oscillation amplitude obtained at a step in the current determination to be within +/−20% (20% is provided as an example) of the oscillation amplitude size as obtained from the curve fit of the last determination. Note also that the curve fit from the last determination may be shifted to handle small changes in blood pressure before use in this tolerance test.

Determining whether the complexes are within a tolerance provides another test as to whether or not a significant physiological change has taken place. Furthermore, a tolerance test based on how well new data approximates a previous curve fit may be an indication of the presence of motion artifact which is not being adequately eliminated by other parts of the algorithm. In such a situation, it might also be necessary to cause a reversion and proceed with smaller deflation steps. Thus, evaluating how close the current pulse amplitudes are to the pulse amplitudes from a previous determination provides a powerful way to help decide if a reversion should be done. If the complexes are within an acceptable tolerance of the last envelope, the process determines at step 212 whether the envelope acquisition process is complete. The algorithm must decide whether an adequate number of pressure steps have been visited for an accurate calculation of blood pressure. If the envelope acquisition is not complete, the process proceeds to step 228 and returns a "No" decision on whether to revert. In other words, the envelope acquisition process would continue to obtain additional points. If the envelope acquisition is complete, the process makes a determination at step 214 as to whether these data points are adequate to compute the blood pressure. Thus, if the algorithm finds that enough pressure steps have been visited for a blood pressure determination, the final calculation of blood pressure can be made. Generally, to fill out the oscillometric envelope, complexes are measured at cuff pressure steps above systolic, below systolic but above MAP, below MAP but above diastolic and below diastolic. Thus, there should be at least four pressure steps to form an envelope. The data at these four pressure steps, however, can be augmented by data from prior determinations or augmented by predicted amplitudes at specific pressures derived from a prior curvefit. If there are enough points to adequately specify the oscillometric envelope, the process determines whether these points span an appropriate amplitude range on the systolic side of the envelope at step 216 and whether these points span an appropriate amplitude range on the diastolic side at step 220. Typically, there should be at least two steps on either side of the maximum of the oscillometric envelope curve. However, if there are only four points in the current determination, the two points on either side of the maximum can be inclusive of the maximum point. If there are enough points on the diastolic and systolic sides, then the process returns a "No" decision on whether to revert at step 228.

When deciding to make a reversion, it is often necessary to make sure the shift in blood pressure is consistent from step to step. This requirement places a multi-step requirement on recognizing the shift before actually reverting. Returning to step 202, if the old envelope shifted more than 10 mm Hg, the process determines at step 204 whether the shift has been consistently present. In other words, a shift greater than 10 mm Hg should be present for at least two steps before triggering a revert. A repeated and consistent shift in the current determination envelope data is a strong indication of a change in blood pressure. If there has been a consistent shift, the process determines whether the consistent shift is positive at step 208. If the shift is positive, a reversion is required with a pump up to a higher cuff pressure than was first used during the current determination. If the consistent shift at step 204 is negative, a reversion is done without a subsequent pump up at step 230. A similar decision is made after gathering what is expected to be a complete envelope. If it is determined that there is not enough diastolic data at step 220, a reversion is necessary, but the need for a pump up at this point is based on the characteristics of the envelope data. The process determines whether the lowest complex size on the diastolic side is less than a predetermined limit (e.g., 50%) of the maximum complex size at step 222. The term "lowest" here refers to the lowest cuff pressure step used in the process up to that point. If the lowest complex size on the diastolic side is less than 50% of the maximum complex size, a determination is made at step 224 to revert at a pressure below the lowest pressure used so far. This may not require a pump up if the cuff pressure step is the lowest that has been used so far in the process. However, if the lowest complex size on the diastolic side is not less than 50% of the maximum complex size, a decision is made at step 226 to revert with a pump up to a pressure above the lowest cuff pressure step visited so far in the process. As one skilled in the art would appreciate, any number of other limits could also be used (i.e., 45%, 55%, etc.). Further, the envelope shift value may be filtered before being compared to the threshold to cause the reversion. This action would make sure that the change in blood pressure is worth responding to with a reversion.

The details of the mathematical process of shifting an oscillometric curve will now be addressed. Although many different forms can be used, an envelope curve fit may be represented according to the following equation:

$$A_i = A e^{-((P_i - B)^2 / C)} = f(P_i; A, B, C)$$

where A, B and C represent parameters which set the amplitude, the mean, and the spread of the envelope. $A_i$ and $P_i$ are the oscillation amplitude and cuff pressure, respectively, of a specific envelope data point. We compute and store the A, B and C parameters from the oscillometric envelope data of a prior blood pressure determination for future use. The envelope shift can be found by taking a new measured point in the current determination ($P_i$, $A_i$) for a given A and C (from previous determination) and inverting the formula to find $B_{new}$. The amount of difference between the $B_{new}$ and the original B is an estimate of the blood pressure shift. The actual inversion and difference formula would then be:

$$Bnew-B=Pi\pm\sqrt{(C\ln(A/Ai)}-B=\text{Envelope Shift}$$

Note that this is just an example for a Gaussian form envelope equation. The plus or minus could be determined by finding which one provides the least shift. If the shift is so large that this technique doesn't cause a reversion when one is necessary, the amplitude tolerance or shape criteria described earlier will eventually cause the reversion. Also, the techniques for inversion to compute the shift could include any number of algorithms. An example might be Newton's method or a more brute force search. Though the described techniques assume a single C (spread) parameter, one could use a different C (spread) parameter on either side of the maximum on the oscillometric envelope as described in U.S. Pat. No. 5,704,362 to Hersh et al. In this event, the shift calculations would incorporate using different C (spread) parameters depending on the location of the pressure step in relation to the oscillometric envelope. An example of the computation of the normalized tolerance may be represented according to the following equation:

$$\text{Tolerance}=|(Ai-f(Pi;A,B,C))/f(P i;A,B,C)|.$$

where A, B and C parameters are from the oscillometric envelope data of a prior blood pressure determination, Ai is the oscillation amplitude being checked, and Pi is its corresponding cuff pressure.

While this equation provides one example for finding a tolerance value, those skilled in the art will realize that a number of other equations or methods could be used. For example, rather than using the curve fit from a previous determination, tolerance could be based on the size of the oscillation amplitude at the closest step available in the last determination or on the maximum oscillation size from the last determination. The tolerance equation above should only be taken as exemplary.

As described herein, if there has not been a shift in the envelope data of more than 10 mm Hg at step 202, the process determines whether the complexes are within a tolerance of the last envelope at step 206. If the complexes are not within an acceptable tolerance, the process determines whether the complexes are consistently and repeatedly out of tolerance at step 210. Typically, for a complex to be consistently and repeatedly out of tolerance, it must exceed the tolerance for two or more steps. In addition, the allowable tolerance can vary depending on location along the oscillometric envelope (i.e., systolic, diastolic, MAP, etc.). If the complex exceeds the tolerance repeatedly, the process determines at step 218 that a reversion is necessary with a pump up to higher cuff pressure. A higher cuff pressure typically means an increase in cuff pressure of about 40 mm Hg above the highest cuff pressure taken in the on-going determination. Of course, 40 mm Hg is merely exemplary and any number of other measurements could also be used (i.e., 35 mm Hg, 45 mm Hg, etc.).

Figure 6:
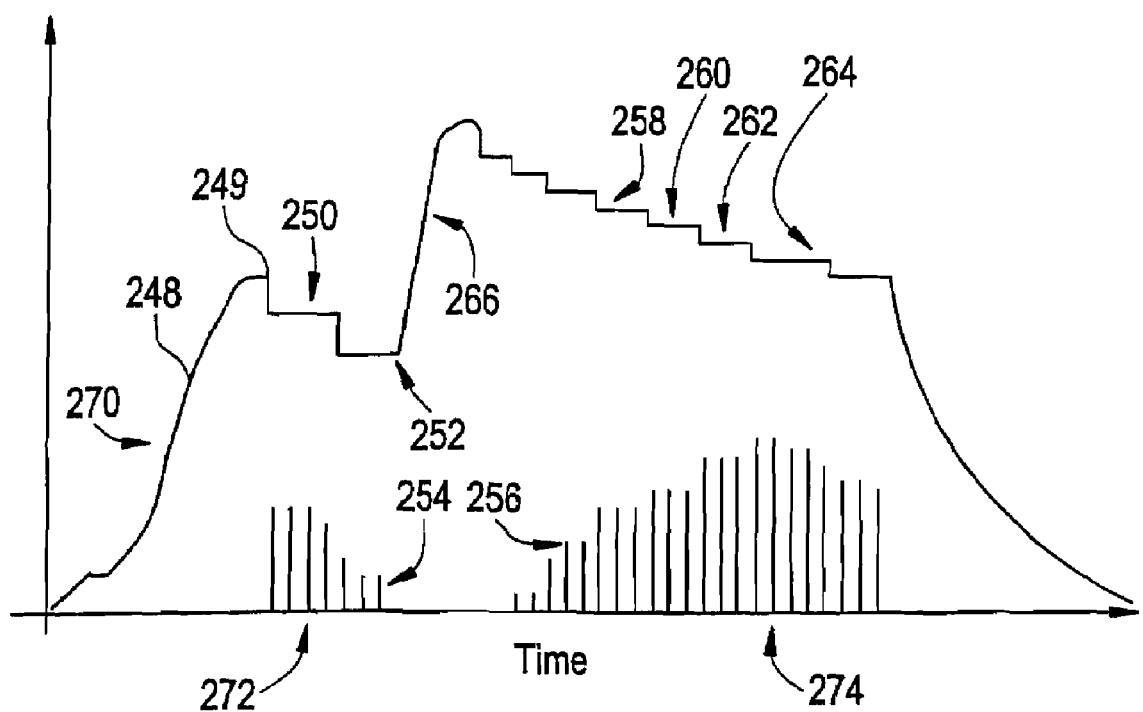
FIG. 6 illustrates cuff pressure and step size control during an oscillometric determination of blood pressure. This figure also illustrates a reversion step according to an embodiment of the present invention.

FIG. 6 shows oscillometric data from a blood pressure measurement when a reversion step is made during the process. Curve 270 represents the overall cuff pressure of the inflatable cuff and curves 272, 274 represent the measured peak pulse amplitudes for oscillometric complexes. The cuff pressure is increased as indicated by the upward curvature of line 248 as the cuff is inflated. Once a chosen pressure is selected at point 249, large deflate steps are initiated, as shown by step 250. After several large steps, it is determined that the measured peak pulse amplitudes for the oscillometric complexes 254 are inappropriate. As is known in the art, when a cuff is inflated to a pressure above a patient's systolic pressure and then incrementally reduced in a series of small steps, the oscillations should begin small and then gradually increase to a maximum. Since the oscillations 254 began at a higher level and then decreased, the determination to revert occurs at point 252. The reversion occurs and the cuff is once again inflated as shown by the upward curvature of line 266. Once a desired pressure is attained, smaller incremental deflate steps 258, 260, 262, 264 begin. The measured peak pulse amplitudes of oscillations 256 more closely follow the expected pattern of blood pressure oscillation amplitudes so that the full range of oscillation measurements are obtained. According to a preferred embodiment, oscillometric data is not purged when doing the reversion. Instead, the new data is filled in to complete the oscillometric envelope.

While the embodiments and application of the invention illustrated in the figures and described above are presently preferred, it should be understood that these embodiments are offered by way of example only. Accordingly, the present invention is not limited to a particular embodiment, but extends to various modifications that nevertheless fall within the scope of this application.

What is claimed is:

1. A method of determining when to make a reversion to smaller cuff pressure steps during an oscillometric blood pressure measurement, comprising:
   inflating a cuff positioned on a subject to an initial inflation pressure;
   obtaining current oscillometric envelope blood pressure data from a pressure transducer in the cuff as the cuff is deflated from the initial inflation pressure;
   comparing conformance of the current oscillometric envelope blood pressure data with previous oscillometric envelope blood pressure data retrieved from a database of previous oscillometric envelope blood pressure data, including evaluating whether oscillometric envelope amplitudes of the current blood pressure data exceed an allowable tolerance from the previous blood pressure data; and
   making a reversion decision based on whether the oscillometric envelope amplitudes exceed the allowable tolerance, wherein the reversion decision deflates the cuff in smaller cuff pressure steps.

2. The method of claim 1, wherein making a reversion decision further includes evaluating whether the oscillometric envelope amplitudes have consistently exceeded the allowable tolerance.

3. The method of claim 1, further comprising evaluating whether an oscillometric envelope acquisition process has been completed, wherein making a reversion decision further includes determining whether the envelope acquisition process has been completed.

4. The method of claim 3, further comprising evaluating whether a sufficient number of oscillometric envelope data points have been obtained on systolic and diastolic sides of the oscillometric envelope blood pressure data.

5. The method of claim 3, wherein making a reversion decision further includes evaluating whether a lowest complex side on a diastolic side of the oscillometric envelope blood pressure data exceeds an allowable threshold in order to decide whether a pressure change should be made.

6. The method of claim 5, wherein the allowable threshold is about 50% of a maximum complex size in the oscillometric envelope blood pressure data.

7. The method of claim 1, further comprising:

measuring a shift between a current oscillometric envelope derived from the current blood pressure data and a previous oscillometric envelope derived from the previous blood pressure data; and making a reversion decision based on whether the shift exceeds an allowable threshold.

8. The method of claim 7, wherein making a reversion decision further includes evaluating whether the shift has been consistently present in the oscillometric envelope blood pressure data.

9. The method of claim 7, wherein making a reversion decision further includes evaluating whether the shift is positive or negative.

10. The method of claim 9, wherein making a reversion decision further includes evaluating whether a lowest complex size on a diastolic side of the oscillometric envelope blood pressure data exceeds an allowable threshold.

11. The method of claim 10, wherein the allowable threshold is about 50% of a maximum complex size in the oscillometric envelope blood pressure data.

12. The method of claim 1, further comprising:

evaluating whether an oscillometric envelope acquisition process has been completed; and making a reversion decision based on whether the envelope acquisition process has been completed.

13. The method of claim 12, further comprising evaluating whether a sufficient number of oscillometric envelope data points have been obtained.

14. The method of claim 12, wherein making a reversion decision further includes evaluating whether a lowest complex side on a diastolic side of the oscillometric envelope blood pressure data exceeds an allowable threshold.

15. The method of claim 14, wherein the allowable threshold is about 50% of a maximum complex side in the oscillometric envelope blood pressure data.

* * * * *